United States Patent [19]

Bredesen

[11] Patent Number: 5,324,654
[45] Date of Patent: Jun. 28, 1994

[54] METHOD FOR REVERSIBLY INCREASING PROLIFERATION OF A NON-MALIGNANT CELL POPULATION

[75] Inventor: Dale E. Bredesen, Los Angeles, Calif.

[73] Assignee: The Regents of the University of California, Oakland, Calif.

[21] Appl. No.: 818,491

[22] Filed: Jan. 8, 1992

Related U.S. Application Data

[63] Continuation of Ser. No. 583,809, Sep. 17, 1990, abandoned.

[51] Int. Cl.$^5$ .................. C12N 5/00; A61K 31/70; C07H 17/00; A01N 43/04
[52] U.S. Cl. .................. 435/240.2; 435/6; 435/172.3; 935/10; 935/23; 935/52; 536/23.1; 536/23.5; 536/23.72; 514/44
[58] Field of Search .................. 435/6, 240.2, 69.4; 935/172.3, 10, 23, 52; 514/44; 536/27, 28, 29

[56] References Cited

U.S. PATENT DOCUMENTS 4,885,238 12/1989 Reddel et al. .................. 435/29

OTHER PUBLICATIONS

Ann Gibbons (1992), Science vol. 256, pp. 766–768.
Jack S. Cohen (Nov. 1989), TIPS, vol. 10, pp. 435–437.
Van der Krol (1988) Biotechniques, 6(10) pp. 958–976.
Hawley-Nelson, P., Vousden, K. et al. "HPV 16 E6 and E7 Proteins Cooperate to Immortalize Human Foreskin Keratinocytes", The EMBO Journal vol. 8, No. 12 pp. 3905–3910, 1989.
Lee, E. Y.-H. P., Bookstein, R. et al., "Molecular Mechanism of Retinoblastoma Gene . . . ", Proc. Natl. Acad. Sci USA vol. 85, pp. 6017–6021, Aug. 1988 Genetics.
Blau, Helen, Webster, C. et al. "Defective Myoblasts Identified in Duchenne Muscular Dystrophy", Proc. Natl. Acad. Sci, U.S. vol. 86, pp. 4856–4860, Aug. 1983.
Buchkovish, K., Duffy, L. A., and Harlow, Ed, "The Retinoblastoma Protein Is Phosphorylated . . . ", Cell, vol. 58, pp. 1097–1105, Sep. 22, 1989.
Cavenee, W. K., Dryja, T. P. et al., "Expression of Recessive Alleles by Chromosomal Mechanisms . . . ", Nature, vol. 305, Oct. 27, 1983.
Werness, Bruce A., Levine, Arnold J., et al., "Association of Human Papillomavirus Types 16", Science, vol. 248, pp. 76–78.
Goodchild, John, "Inhibition of Gene Expression by Oligonucleotides", Oligodeoxynucleotides, pp. 53–77.
Neckers, L. M., "Antisense Oligodeoxynucleotides as a Tool for Studying Cell Regulation: Mechanism of Uptake and Application to the Study of Oncogene Function", Oligodeoxynucleotides, pp. 211–231.
Hayflick, L., "The Limited In Vitro Lifetime of Human Diploid Cell Strains", Experimental Cell Research 37, pp. 614–636 (1965).
Di Fiore, P. P., Segatto, Oreste et al., "EGF Receptor and erbB2 Tyrosine Kinase Domains Confer Cell Specificity for Mitogenic Signalling", Science Reports, pp. 79–84, vol. 248, Apr. 6, 1990.
Ludlow et al. (1989), cell vol. 56 pp. 57–65.
Lee et al. (1987), Nature, vol. 329 pp. 642–645.
Becker et al. (1989), the EMBO Journal vol. 8, #12, pp. 3685–3691.
Khokha et al. (1989), Science, vol. 243 pp. 947–950.
Huang et al. (1988), Science vol. 242 pp. 1563–1566.
Hu et al. (Apr. 1990), the EMBO Journal vol. 9 No. 4, pp. 1147–1155.

Primary Examiner—Robert J. Hill, Jr.
Assistant Examiner—Gian P. Wang
Attorney, Agent, or Firm—Poms, Smith, Lande & Rose

[57] ABSTRACT

A method and composition for reversibly increasing the proliferation of cells in vitro. Cell populations are treated in vitro with antisense oligonucleotides to a tumor suppressor gene, such as the retinoblastoma (Rb) gene. Such treatment inhibits expression of the tumor suppressor gene product and results in a reversible increase in the proliferation of the cell population.

4 Claims, No Drawings

METHOD FOR REVERSIBLY INCREASING PROLIFERATION OF A NON-MALIGNANT CELL POPULATION

This is a continuation of copending application Ser. No. 07/583,809 filed on Sep. 17, 1990, now abandoned.

BACKGROUND OF THE INVENTION

1. Field of the Invention

The present invention relates generally to methods and compositions that are used to control the rate at which cells proliferate and their capacity for proliferation. More particularly, the present invention involves methods and compositions which are used to increase cell proliferation in a completely reversible way without causing the cells to become malignant or otherwise affecting the cells.

2. Description of Related Art

Many diseases involve the degeneration of specific cells. Such diseases include Duchenne's muscular dystrophy, insulin dependent diabetes mellitus, Parkinson's disease, Huntington's disease, Alzheimer's disease, olivopontocerebellar atrophy and many others. A suggested treatment for these diseases involves removing cells from relatives and introducing them into the patient. However, rejection of the foreign cells is and will be a recurrent problem with such a proposed treatment approach (Partridge, T.A., et al. (1989)). Nature 337:176–179). (Another approach to treating the above-identified diseases is to use the patient's own cells. Use of the patient's own cells allows a perfect immunological match and therefore overcomes any problems associated with rejection of the cells. In such processes, the patient's cells are removed from the patient, grown in vitro, genetically engineered to produce the appropriate protein, and reintroduced to the patient.

A major problem with the above approach is that tumor suppressor genes are expressed in all normal (non-cancerous) cells. These tumor suppressor genes express proteins that inhibit growth of cells. Viruses and transforming genes have been used to bind the inhibiting proteins and thereby effect proliferation of cells.

SUMMARY OF THE INVENTION

In accordance with the present invention, a method for increasing non-malignant proliferation of a cell population is provided wherein expression of a tumor suppressor gene product, such as the Rb gene product, is specifically and reversibly inhibited in vitro without the use of viruses or oncogenes. The present invention is based upon the discovery that treatment of in vitro cell productions with antisense oligonucleotides to a tumor suppressor gene, such as the Rb gene, specifically and reversibly inhibits expression of the gene product. As a result, the non-malignant proliferation of the cell population is increased.

As a feature of the present invention, the cell population is treated in vitro with antisense oligonucleotides having from 8 to 30 nucleotides which are antisense to a portion of the first 30 nucleotides of the open reading frame of human Rb mRNA. These particular antisense oligonucleotides provide specific and reversible inhibitions of Rb gene product expression in a variety of cell types. For example, the present invention is useful in increasing non-malignant proliferation of cell populations including human and non-human fibroblasts, keratinocytes, glioblasts, hepatic cells, renal cells, pancreatic islet cells, myoblasts, neuroblasts, and endothelial cells. These cell populations, when treated with the antisense oligonucleotides in accordance with the present invention, experience increased and completely reversible proliferation.

As another feature of the present invention, two specific antisense oligonucleotides are disclosed which are effective in reversibly and specifically inhibiting the production of Rb gene product. The two antisense oligonucleotides have the nucleotide sequences 3'-TACGGCGGGTTTTGG-5' and 3'-GGGGCTTTTTGCCGG-5'. These two antisense oligonucleotides, when disbursed in a pharmaceutically suitable carrier provide a composition which is useful in the treatment of cell population to increase non-malignant proliferation.

The present invention is also useful in treating patients for a variety of diseases involving cell degeneration. For such patients, a specific cell population is removed from the patient, treated in vitro in accordance with the present invention to proliferate the cells and returned to the patient. If desired, the cell population which is proliferated in vitro may be genetically engineered to replace a missing gene product prior to re-implantation. The above discussed and many other features and attendant advantages of the present invention will become better understood by reference to the following detailed description.

DETAILED DESCRIPTION OF THE INVENTION

The present invention is useful in increasing non-malignant proliferation of a wide variety of cell populations or cultures. Typical cell populations which can be proliferated in accordance with the present invention include human and non-human fibroblasts, keratinocytes, glioblasts, hepatic cells, renal cells, pancreatic islet cells, myoblasts, neuroblasts, and endothelial cells. All of these cells include tumor suppressor genes which express retinoblastoma (Rb) gene product. The present invention involves treating these cell populations in vitro with antisense oligonucleotides which inhibit the expression of the Rb gene product by the cells. As a result, proliferation of the cell population is increased without rendering the cells cancerous.

In order to carry out the present invention, the cell population or culture must be maintained in vitro under normal conditions which promote cell proliferation and growth. The various culture media and conditions which are necessary to promote such growth will vary widely depending upon the type of cell population being treated. The conditions required for in vitro culturing and growth of cell populations are well known for individual cell types and will not be described in detail.

In accordance with the present invention, the existing in vitro cell culture or population is treated with a sufficient amount of antisense oligonucleotide to inhibit expression of Rb gene product by the tumor suppressor genes of the cells. The treatment of cells with antisense oligonucleotides is a procedure which is described in detail in Cohen JS (ed): Oligonucleotides: Antisense Inhibitors of Gene Expression. CRC Press Inc., Boca Raton, Fla., 1989.

The oligonucleotides which are suitable for use in accordance with the present invention must include sufficient antisense nucleotides to inhibit expression of the Rb gene product by the human Rb mRNA. Preferably, the antisense oligonucleotide will include from between 8 to 30 nucleotides which are antisense to a portion of the first 30 nucleotides of the open reading frame of human Rb mRNA. Human retinoblastoma (Rb) mRNA has been studied by many investigators and its nucleotide sequence is well known (Lee, E-Y, et al. Proc. Natl. Acad. Sci. USA 1988;85, 6017–6021). Two preferred antisense oligonucleotides have the sequence 3'-TACGGCGGGTTTTGG-5' and 3'-GGGGCTTTTTGCCGG-5'. Other antisense oligonucleotides can be utilized provided that they inhibit expression of the Rb gene product. These include oligodeoxynucleotides (normal, phosphorothioates, methylphosphonates, or other derivatives) and oligo(ribo)nucleotides, as well as ribozymes.

Administration of the antisense oligonucleotides to the cell culture is accomplished in accordance with known procedures. Typically entry into the cells may be achieved by bathing the cells in medium containing 5 uM to 200 uM or more antisense oligonucleotides (less may be required for some of the modified oligonucleotides), by encapsulating the oligonucleotides in lipsomes or red cell ghosts, or by injecting the oligonucleotides into the cells. Antibodies or ligands may be used to target the oligonucleotide-filled liposomes to specific cells.

The present invention may be used generally to increase non-malignant proliferation of cell populations in vitro. However, the invention is especially useful in treating diseases where specific cells degenerate. These diseases include Duchenne's muscular dystrophy, insulin dependent diabetes mellitus, Parkinson's disease, Huntington's disease, Alzheimer's disease, Olivopontocerebellar atrophy and many others. Treatment of these diseases in accordance with the present invention involves removing the patient's cells and proliferating them in vitro utilizing the antisense oligonucleotide procedure previously described. The proliferated cells are then reimplanted directly into the patient or genetically engineered to replace missing gene products, such as dystrophin in Duchenne's muscular dystrophy. The proliferated genetically engineered cells are then reimplanted.

The following are examples of practice:

Human fibroblasts (ATCC #CRL 1477) at the 16th passage were seeded onto 96 wheel plates at densities of 2000; 5000; 10,000 and 20,000 per well. They were cultured in Dulbecco's modified Eagle's medium (DME; Whittaker Bioproducts) with 10% fetal bovine serum (FBS) at 37° C. and 5% $CO_2$. After allowing 16 hours for cell attachment, the cells were treated with either 0, 5, 10, 15, 20, 30, or 40 uM concentrations of each of the two continuous antisense oligodeoxynucleotides which have been previously described. These two oligonucleotides have been labelled HRB-1 and HRB-2 and are set forth in the Table below along with the relevant portion of the Rb gene.

added in serum-free medium to a volume of 35 ul per well. After an additional 32 hours, the antisense oligodeoxynucleotides were reapplied at the same concentrations. Thirty-two hours later, three assays were carried out. The assays were: (1) the dimethylthiazol diphenyl tetrazolium bromide (MTT) assay (T. Mosmann, J. Imm Methods. 65, 55 (1983)); (2) bromodeoxyuridine (BrdU) incorporation; and (3) cell count. The BrdU assay was determined by using monoclonal antibody (Amersham, Inc.) to detect incorporated bromodeoxyuridine.

The results for all three assays were no different for untreated cells than for cells treated with the control antisense oligodeoxynucleotide at 0–30 uM. In contrast, when the cells were treated with a combination of 15 uM of each of the two antisense oligodeoxynucleotides to the Rb mRNA, the MTT assay revealed an increase in formazan production, as measured spectrophotometrically. The magnitude of the increase was dependent on the antisense concentration and the number of cells seeded, reaching a maximum of 50%. That this increase was due to increased mitosis was confirmed by both BrdU incorporation and cell counts. The BrdU incorporation increased threefold in the cells treated with antisense oligonucleotides to the Rb mRNA. The increase in BrdU incorporation occurred within 24 hours of antisense application, and abated after 48 hours. This increased mitotic rate was reflected in an increased cell number.

A concentration dependence was observed for the effect of the antisense oligonucleotides on both BrdU incorporation and cell numbers. The maximal effect occurred at 20 uM total oligonucleotide concentration (10 uM for each of HRB-1 and HRB-2). At concentrations of 60 uM and above, all oligodeoxynucleotides used in this study appeared to be cytotoxic based on decreases in BrdU incorporation and formazan production from MTT. The 60 uM cutoff may be increased by further purifying the oligodeoxynucleotides.

To determine the effects of the antisense oligonucleotides on cellular Rb levels, immunofluorescent staining of treated and untreated cells was carried out, using a monoclonal antibody directed against human Rb (Monoclonal antibody Mh-Rb-02 from Pharmingen). This antibody binds to both phosphorylated and unphosphorylated forms of Rb. Nuclear staining was observed in all cells of the untreated group, but was markedly reduced in the cells treated with RB 1 antisense oligonucleotides.

Identical procedures were carried out using antisense oligodeoxynucleotides to two other putative tumor suppressor genes, p53 (R. Zakut-Houri, B. Bienz-Tadmor, D. Givol, M. Oren, EMBO J. 4, 1251 (1985)) and DCC (E.R. Fearon et al., Science 247, 49 (1990)). For p53 as for Rb, two 15-mers antisense to the first 30 nucleotides of the open reading frame were synthesized. For DCC, because of potential interoligonucleotide

TABLE

5'-AGGCGTCATGCCGCCCAAAACCCCCCGAAAAACGGCCGCCACCGCC-3'
Rb mRNA

3'-TACGGCGGGTTTTGG-5'
HRB-1

3'-GGGGCTTTTTGCCGG-5'
HRB-2

The antisense oligonucleotides (HRB-1 and HRB-2), along with the relevant portion of the Rb gene were hybridization between DCC antisense and Rb antisense, two 15-mers were synthesized that were antisense to nucleotides -6 to +24 with respect to the initiator AUG (14). Numbered with respect to the initiator AUG, the Rb antisense nucleotides, #23-28 (3'-AAACCC-5') are complementary to DCC antisense nucleotides #7-12 (3'-GGGTTT-5'). Antisense to the p53 mRNA at 30 uM and to DCC at 10-30 uM resulted in increases in the MTT assay similar to those resulting from RBI antisense. However, unlike with the RBI antisense, antisense to p53 and DCC mRNA did not alter BrdU incorporation or cell numbers. Antisense to DCC did, however, effect cellular hypertrophy, manifested by in an increased protein content per cell and an increased cell size by flow cytometry.

These, above results show that a decrease in the level of Rb leads to cellular proliferation which is non-maglignant in accordance with the present invention. Similar experiments have been carried out with myoblasts and neuroblasts. Moreover, since Rb is present in all cell types, and since it is well known that virus products that bind these ubiquitous tumor suppressor gene products effect the immortalization of virtually all cell types (Frederiksen D, et al. Neuron 1988; 1:439-448 and Werness BA, Levine AJ, Howley PM. Association of human Papillomavirus Types 16 and 18 E6 Proteins with p53. Science 1990; 248:76-83) it is expected that the same antisense effect will occur in other cells. Furthermore, it is expected that in some cell types, better growth will be obtained by inhibiting simultaneously more than one tumor suppressor gene. For example, by increasing division through Rb antisense and increasing metabolism through DCC antisense; or by a combination of antisense to two tumor suppressor genes to increase proliferation.

The reference articles which are referred to in this specification are hereby incorporated by reference.

Having thus described exemplary embodiments of the present invention, it will be understood by those skilled in the art that the above disclosures are exemplary only and that the present invention is only limited by the following claims. The articles and other references referred to in this specification are hereby incorporated by reference.

I claim:

1. A method for increasing proliferation of a non-malignant cell population wherein the cells of said cell population include tumor suppressor genes which express a human retinoblastoma Rb tumor suppressor gene product, said method comprising the step of treating said cell population in vitro with a sufficient amount of antisense oligonucleotide to human retinoblastoma Rb mRNA to inhibit expression of said human retinoblastoma Rb tumor suppressor gene product by said tumor suppressor gene, to thereby increase non-malignant proliferation of said cell population.

2. A method for reversibly increasing proliferation of a cell population according to claim 1 wherein said cell population comprises cells selected from the group consisting of human and non-human fibroblasts, kerotinocytes, glioblasts, hepatic cells, renal cells, pancreatic islet cells, myoblasts, neuroblasts, and endothelial cells.

3. A method for reversibly increasing proliferation of a cell population according to claim 1 wherein said antisense oligonucleotide includes between 8 to 30 nucleotides which are antisense to a portion of the first 30 nucleotides of the open reading frame of human retinoblastoma mRNA.

4. A method for reversibly increasing proliferation of a cell population according to claim 3 wherein said antisense oligonucleotide has the nucleotide sequence selected from the group consistity of 3'-TACGGCGGGTTTTGG-5' or 3'-GGGGCTTTTTGCCGG-5'.

* * * * *

UNITED STATES PATENT AND TRADEMARK OFFICE
CERTIFICATE OF CORRECTION

PATENT NO. : 5,324,654
DATED : June 28, 1994
INVENTOR(S) : Dale E. Bredesen

It is certified that error appears in the above-indentified patent and that said Letters Patent is hereby corrected as shown below:

In column 1, line 8, before the heading "BACKGROUND OF THE INVENTION", please insert the following:

--This invention was made with support under Grant Number 1 R29 N527812-01 from the National Institute of Health. Accordingly, the U.S. Government has certain rights in the invention.--

Signed and Sealed this

First Day of November, 1994

Attest:

BRUCE LEHMAN

*Attesting Officer*  *Commissioner of Patents and Trademarks*